United States Patent [19]
Soldner et al.

[11] 3,974,682
[45] Aug. 17, 1976

[54] ULTRA SOUND EXAMINING DEVICE
[75] Inventors: Richard Soldner, Erlangen; Rudolf Rattmann, Herzogenaurach, both of Germany
[73] Assignee: Siemens Aktiengesellschaft, Munich, Germany
[22] Filed: Mar. 5, 1975
[21] Appl. No.: 555,359

Related U.S. Application Data
[63] Continuation-in-part of Ser. No. 367,145, June 5, 1973, Pat. No. 3,902,357.

[52] U.S. Cl.................................. 73/67.7; 73/67.9
[51] Int. Cl.² ........................................ G01N 29/04
[58] Field of Search............ 73/67.7, 67.8 R, 67.8 S, 73/67.9

[56] References Cited
UNITED STATES PATENTS

| | | | |
|---|---|---|---|
| 2,467,301 | 4/1949 | Firestone | 73/67.9 |
| 2,682,766 | 7/1954 | Van Valkenburg | 73/67.9 |
| 3,690,154 | 9/1972 | Wells et al. | 73/67.9 |

*Primary Examiner*—Herbert Goldstein
*Assistant Examiner*—John P. Beauchamp
*Attorney, Agent, or Firm*—Richards & Geier

[57] ABSTRACT

An ultra sound examining device operating according to the impulse echo process and used for medical purposes comprises an ultra sound sending-receiving system the sender of which transmits ultra sound impulses in predetermined time intervals into the object being examined through a precursor stretch connected in front of the system, for example, water precursor stretch. There is also an echo impulse representing device operated depending upon the transmitted impulses which represents echo impulses of each transmitted impulse received by the receiver one after the other corresponding to the time sequence of their appearance. The invention is particularly characterized in that the time interval between two successive transmitted impulses of the ultra sound sender has a value which is smaller than the sum of the precursor time of the ultra sound impulses in the precursor stretch and the representation time of the echo impulses on the representing device. However, even the smallest value is not less than the representation time.

3 Claims, 3 Drawing Figures

ULTRA SOUND EXAMINING DEVICE

This application is a continuation in part of the co-pending patent application Ser. No. 367,145, filed June 5, 1973 now U.S. Pat. No. 3,902,357.

This invention relates to an ultra sound examining device operating according to the impulse echo process and used particularly for medical purposes. The device includes an ultra sound sending-receiving system the sender of which transmits ultra sound impulses in predetermined intervals into the object being examined through a precursor stretch connected in front of the system, for example, a water precursor stretch. The device also includes an echo impulse representing device operated depending upon the transmitted impulses which represents as images echo impulses of each transmitted impulse received by the receiver one after the other corresponding to the time sequence of their appearance.

The time period in which the echo impulse representing device represents echo impulses pertaining to a transmitted impulse, is described hereinafter as the representation time.

Devices of this type are used as so-called A-scan or B-scan devices for example, for examination of materials or in medical diagnosis to investigate or to make an image of internal body layer structures, for example, pictures of sections through internal organs or the like. The switching of a precursor stretch between the ultra sound sending-receiving system and the object being examined, on the one hand makes possible the work in the remote zone of the system in which there are specific intensity relations within the direction characteristic of the ultra sound sender. On the other hand it serves to eliminate image falsifying multiple echoes from the image range of the echo imagery. Cathode ray tubes are generally used for the representation of echo impulses whereby depending upon the use (B-scan or A-scan) the electronic ray of the tube is deviated depending upon the ultra sound transmitted impulses either line by line over the R.C. tube screen or merely periodically over its time axis; the representation of the echo impulses takes place by intensity modulation or analogous vertical deviation of the electronic ray whenever an an echo impulse is received. The normal time period of a sending or representing cycle in known devices is one which corresponds to the specific time period after transmitting an ultra sound impulse. This time period corresponds to the precursor time period of the ultra sound impulses in the precursor stretch. The normal time period of the cycle releases a line for line movement or a time deviation of the electronic ray of the tube (beginning of the representation time), whereby during this line by line movement or during this time axis deviation the echo impulses pertaining to the transmitted impulse will be represented. Furthermore, at the end of the line by line movement or time axis deviation (end of representation time) a new impulse is transmitted and thus a further transmitting and representing cycle is started.

A transmitting and representing cycle with this time sequence has substantial drawbacks in view of the usually long precursor stretches in known devices. It is known that to properly eliminate multiple echoes from image representation the precursor stretch must be at least somewhat longer than the desired maximum representation depth in the region being examined. The drawback is that long precursor stretches extend the precursor time period of ultra sound impulses so that the ineffective time period between the transmitting of impulse rays and the representation of corresponding echo impulses is increased and thus image representation upon the C.R. tube screen is undesirably delayed. The term "multiple echoes" is used herein to describe echoes which come from the examining object to the receiver and are partly reflected back to the object and then again reach the receiver.

An object of the present invention is to eliminate such drawbacks by providing a device of the described type wherein despite long precursor stretches the imaging takes place faster than in known devices.

Other objects of the present invention will become apparent in the course of the following specification.

In the accomplishment of the objectives of the present invention it was found advisable to provide a device of the decribed type wherein the time interval between two sent impulses of the ultra sound sender which follow each other, has a value which is smaller than the sum of the precursor time of the ultra sound impulses in the precursor stretch and the representation time of the echo impulses on the image representing device. However, even the smallest value should not be less than the representation time.

In the device of the present invention the transmitting of a further ultra sound impulse does not take place only after termination of an echo impulse representation pertaining to the previous transmitted impulse, but at an earlier time still located in the transmitting or representation cycle of this preceding transmitted impulse. Thus image formation on the R.C. tube screen is faster than in known devices.

In devices of the present invention wherein the precursor time of ultra sound impulses is at least equal to the representation time of echo impulses, the present invention provides that time intervals between transmitted impulses are advantageously so selected that already during the precursor time the representing device is at least once activated to provide a complete representation of echo impulses. This selection of time intervals of transmitted impulses at least doubles the speed of image formation as compared to known devices. If in addition the transmitted impulse repetition frequency is swept in frequency which means that the (normally constant) repetition frequency of transmitted impulses, for example at 2kc/s, is frequency-modulated, for example with a sweep frequency of 50 c/s for characterizing such multiple echoes, which are possibly not yet eliminated despite the use of precursor stretch such multiple echoes appear in image representation as light points moving back and forth with the sweep frequency, then advantageously the representing device is always activated depending upon the transmitted impulse the echo impulses of which are to be represented. The proper time activation takes place by the transmitted impulse supplied to the representation device with a delay by the precursor time or by an activating signal produced depending upon the transmitted impulse and delayed relatively to its appearance time by the precursor time period. On the other hand if the time spaces of the transmitted impulses are constant, then the activation of the representing device can take place also without delays by each individual transmitted impulse directly at the time or after its appearance.

In case of delayed activation advantageously pulse running chains or monostable multivibrators are used for delayed supply of transmitted impulses to the representing device or for delayed producing of activating signals. In devices wherein the time spacing between the transmitted impulses is selected to be smaller than the precursor time in the precursor stretch and wherein the impulse repetition frequency is swept in frequency, the delayed activation of the representing device can be carried out in accordance with the present invention be with simplest and cheapest means by a total of two monostable multivibrators which alternately are triggered by successive transmitted impulses and which produce with each triggering a voltage impulse of the duration of the precursor time period, the end of which releases the activation. A bistable multivibrator is connected in front of said multivibrators and is switched alternately in time with the transmitted impulses from its one stable condition to its other stable condition, whereby during change into one stable condition it triggers one monostable multivibrator and during change into the other one of the stable conditions it triggers the other monostable multivibrator. This delay switch circuit consisting of two monostable multivibrators and one bistable multivibrator provides that each individual transmitted impulse will positively actuate the representing device after the desired delaying time. In accordance with the present invention the best image repetition frequencies are produced for precursor time periods which are smaller than the double echo impulse representation time by selecting the average time interval between two successive transmitted impulses to be equal to the sum of the regular echo representation time, the transmitted impulse width and (when repetition frequency of transmitted pulses is swept) of at least one half of the frequency sweep width.

The invention will apear more clearly from the following detailed description when taken in connection with the accompanying drawings showing by way of example only, a preferred embodiment of the inventive idea.

In the drawings:

FIG. 1 is a diagrammatic sectional view of an ultra sound sending-receiving system with a precursor stretch for an ultra sound examining device of the present invention.

FIG. 2 shows a diagrammatic switch circuit of an embodiment of the ultra sound examining device of the present invention with an ultra sound sending-receiving system according to FIG. 1 as well as a cathode ray tube as the image producing device for the echo impulses.

Figure 3:
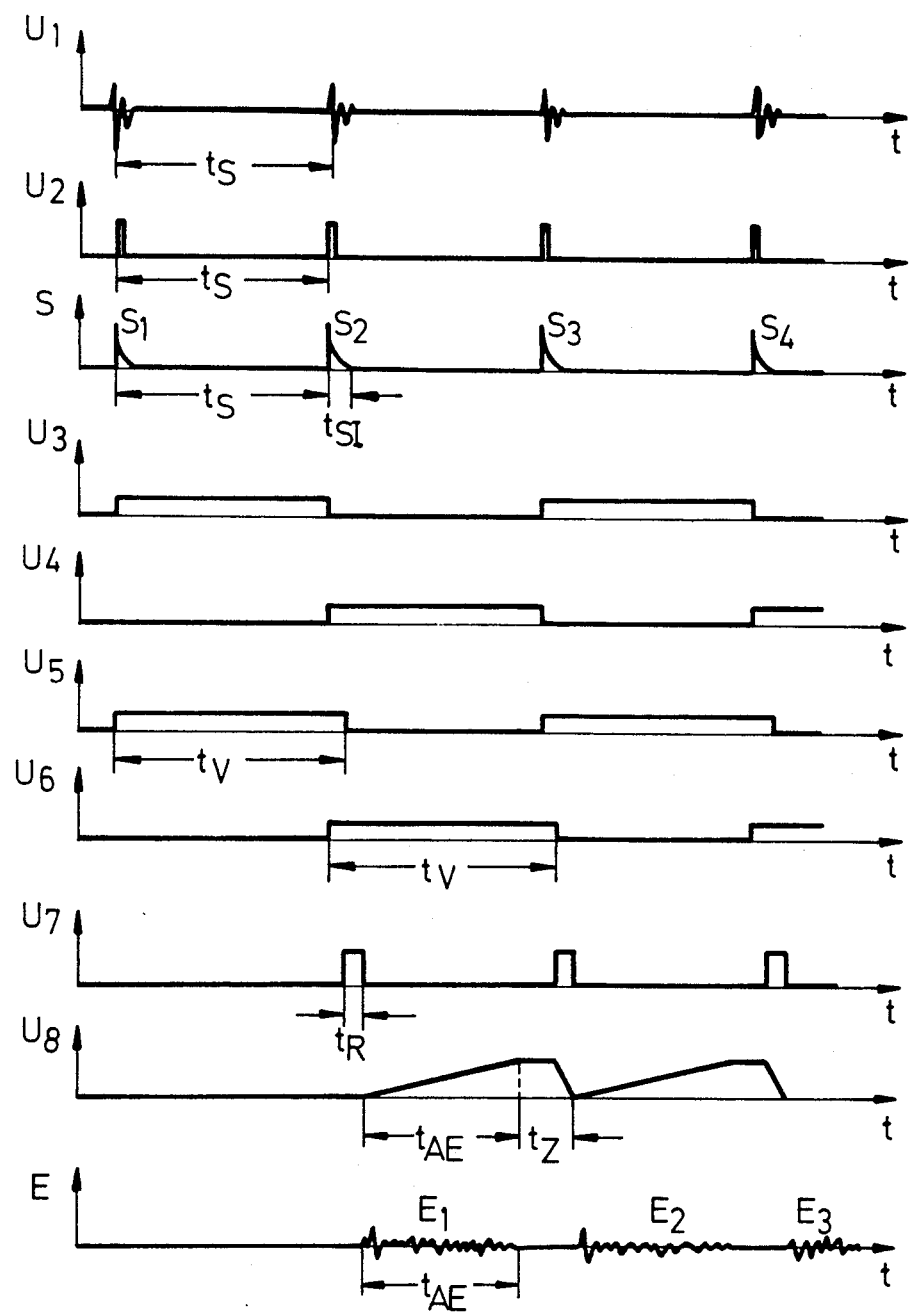
FIG. 3 shows diagrams of variations in time of important voltages appearing at different locations of the circiut of FIG. 2.

FIG. 1 shows an ultra sound sending-receiving system 1 which is located in the focal line 2 of a cylindrical parabolic reflector 3 and is rotatable about this focal point as axis in the direction of the arrow 4. The system 1 and the reflector 3 are completely located in a container 5 filled with water, which is sealed by a sealing diaphragm 6 with reference to the object 7 being examined, such as a human body. When the system 1 is operated the sender of this system transmits ultra sound impulses in the direction toward the reflector 3, from which they are reflected and radiated into the body 7. The radiation of the ultra sound transmitted impulses, such as $S_1$, $S_2$, upon the reflector 3 can take place with immovable system 1. The path of the impulses through water, indicated by the broken line 8 and through the object, indicated by the line 9, is then always the same (A-scan process). However, the radiation of impulses can also take place with a quickly rotating system 1. Then the ultra sound ray radiated into the object 7 being examined will be shifted parallel to itself, namely, the object 7 being examined will be scanned linewise by the ultra sound impulses (B-scan process). The parallel shifting is indicated by a further ray path 10, 11. The ultra sound transmitted impulses radiated into the object 7 (for example, $S_1$ and $S_2$) produce in the object 7 reflection impulses E at different tissue layers. These reflected impulses (for example, $E_1$ and $E_2$) are received after each impulse transmitting by the system 1 switched over to reception and, for example, are transmitted to an oscillograph tube for representation.

In the embodiment of the ultra sound system of FIG. 1, in order to eliminate multiple echoes, the stretch in water of the ultra sound impulses (broken lines 8 and 10) is shown as being somewhat longer than the desired maximum representation depth (for example, lines 9 and 11) in the object 7 being examined (echoes from this depth should be just suitable for representation). In the following description of FIGS. 2 and 3, the precursor time of impulses in the water container (sum of running time of the transmitted impulses from sender to the diaphragm 6 and of the echo impulses from the diaphragm 6 to the receiver) is indicated as $t_v$ and the representation time of echo impulses at the representing device (oscillograph tube) at $t_{AE}$.

In FIG. 2 the sender of an ultra sound sending-receiving system 1 of FIG. 1 is indicated as 12 and the receiver as 13 (the sender and receiver, as shown, can consist of two separated piezoelectrical small crystal plates or they can consist of a single piezoelectrical crystal operating alternately as sender and receiver). The sender 12 is connected to a high frequency generator 14 which supplies to the sender 12 high frequency impulses $U_1(t)$ according to FIG. 3. Each high frequency impulse produced by the generator 14 causes the delivery of an ultra sound impulse $S(t)$ through the sender 12 according to FIG. 3. The repetition frequency of the impulses $U_1(t)$ and $S(t)$ can be swept in frequency for example with 50 c/s by a sweeping oscillator device 15. The average time space $t_S$ between two successive impulses $U_1(t)$ or $S(t)$ then corresponds to the sum of the desired echo impulse representation time $t_{AE}$, the impulse width $t_{SI}$ of the ultra sound transmitted impulse $S(t)$ as well as an additional time $t_Z$ which corresponds to the transmission time from one echo impulse representation to the next one and in which is taken into consideration the frequency sweep width ($\pm 25$ c/s at a sweep frequency of 50 c/s) and in a possibly changing precursor stretch also the variation of the precursor time. Ultra sound impulses reflected in the object being examined (for example, object 7) are received as echo impulses $E(t)$ (FIG. 3) by receiver 13 of the system 1 and after being amplified in the amplifier 16 are transmitted to the cylinder 17 of a cathode ray tube 18. Each echo impulse striking the Wehnelt cylinder 17 makes bright for a short time the electronic ray of the tube 18.

The proper successive representation of echo impulses of a transmitted impulse at the tube screen 19 takes place depending upon the entry time period of the corresponding transmitted impulse by a release signal $U_7(t)$ according to FIG. 3, the creation of which is delayed by the precursor time period $t_v$ of the impulses in the water container 5, for the release of horizontal deviation of the electronic ray. The delayed release of electronic ray deviation takes place by an impulse delay device 20 switched by high frequency generator 14 and consisting of a bistable multivibrator 21, two (or more) monostable multivibrators 22 and 23 separately connected to the two outlets of the bistable multivibrator 21, as well as another monostable multivibrator 24 connected behind the monostable multivibrators 22, 23. The bistable multivibrator 21 is alternately switched from one stable condition to another stable condition in measure by actuating impulses $U_2(t)$ according to FIG. 3 produced by high frequency impulse generator 14 from high frequency impulses $U_1(t)$ or ultra sound transmitted impulses $S(t)$. The switch impulses $U_3(t)$ and $U_4(t)$ located at the two outlets of the multivibrator 21 strike with their positive rising flank alternately the monostable multivibrator 22 or 23. Each struck multivibrator 22 or 23 produces at its outlet a voltage impulse $U_5(t)$ or $U_6(t)$ according to FIG. 3 of the duration of the precursor time $t_v$. The monostable multivibrator 24 is struck with the end of a voltage impulse $U_5$ or $U_6$ and it produces for the horizontal deflecting generator 25 of the cathode ray tube 18 the trigger impulse $U_7(t)$ the duration $t_R$ of which is variable for changing the additional time $t_z$. The deviating generator 25 produces a saw tooth voltage $U_8(t)$ according to FIG. 3 at the horizontal deviating plate pair 26 of the tube 18 with the yield of a trigger impulse $U_7(t)$ at the multivibrator 24, whereby the voltage $U_8(t)$ deviates the electronic ray of the tube in horizontal direction over the tube diaphragm 19 with a speed corresponding to the running speed of ultra sound impulses in the object being examined. The time period from the beginning of a horizontal deviation of the electronic ray to the time period of the maximum deviation corresponds to the desired representation time period $t_{AE}$ of the echo impulses, so that all echo impulses dropping during this time period on the Wehnelt cylinder 17 of the tube 18 are represented as spaced in time points of light.

A further saw tooth generator 28 is switched to the vertical pair of deviating plates 27 which in case of B-scan operation deviates the electronic ray of the tube 18 in time synchronization with the rotary drive 29 for the ultra sound sending-receiving system 1 with a speed corresponding to the speed of the parrallel shifting of the ultra sound sent ray in the object 7 being examined, the deviation taking place in vertical direction over the screen 19. In this manner an echo image formed of lines is produced on the C.R. tube screen 19, which shows the inner structure of the sectional surface of the object 7 being examined which had been felt line by line with the ultra sound ray.

As clearly indicated in the voltage diagram of FIG. 3, in the described embodiment of the present invention the time interval $t_S$ between successive transmitted ultra sound impulses $S(t)$ corresponds substantially to the total duration of a horizontal deviation of the electronic ray of the tube 18 over the tube screen 19. Since each impulse transmitted after the time $t_v$ which is only a little larger than distance $t_S$ between the transmitted impulses, releases a horizontal deviation of the electronic ray, it follows that the ultra sound examining device according to FIGS. 1 to 3 of the present invention produces an image representation twice as quickly as the known ultra sound examining devices.

An increase in the number of representations produces a better image reproduction quality for the following reasons:

An observer desires an image flow which should be continuous without any great image flickering. As is known, such an image flow takes place at an image sequence frequency of about 24 images per second. Due to physiological and physical reasons, the ultra sound period in the human body amounts to about 250μsec. The water precursor time period for scattering disturbing multiple echoes must be at least equally long. This produces a total running time of about 500μsec. which results in a maximum of 120 lines per image and a maximum image frequency of 16 images per second. This is a comparatively small image release with image flickering due to low image frequency.

The device of the present invention avoids all these drawbacks as follows:

a. The repetition frequency of the ultra sound sender is so set that the time period ($t_S$) between successive transmitted impulses is at all times smaller than the sum of the precursor time ($t_v$) and the representation time ($t_{AE}$), but is at least as long as the representation time ($t_{AE}$).

b. At the same time, actuating means control the representing device depending upon the impulses of the sender in such manner that the echo impulses ($E_1$, $E_2$, $E_3$ ...) of a transmitted impulse ($S_1$, $S_2$, $S_3$ ...) are represented in the precursor stretch always directly during the precursor time ($t_v$) of the following transmitted impulses ($S_2$, $S_3$, $S_4$ ...).

An increase in repetition frequency according to a) results in that the body being examined is more quickly tested with impulses during a time unit, and thus, echo impulses follow each other correspondingly faster. For example, when image frequency remains the same, the image line number can be doubled to 240 lines. This results in a higher image release degree. However, in case of direct examination, it is advisable to keep the line number smaller. Then, there is a correspondingly higher image-following frequency up to about 35 images per second. There is no image flickering.

The control according to b) prevents overlappings in echo signal indication, as indicated in FIG. 3.

What is claimed is:

1. An ultra sound examining device, particularly for medical purposes, operating according to the impulse-echo process, said device comprising an ultra sound sending and receiving system having an ultra sound sender and a receiver, a precursor stretch, such as water delay coupling means connected to the front of said ultra sound sending and receiving system, an echo impulse representation device, such as a cathode ray tube, and an actuating means connecting said ultra sound sending and receiving system with said echo impulse representation device, wherein said ultra sound sender comprises energizing means for energizing said sender to transmit successive impulses which are spaced in time from each other by a value which is smaller than the sum of the precursor time of ultra sound impulses in the precursor stretch and the representation time of echo impulses on the representation device, but the smallest value being not less than the representation time, and wherein said actuating means actuate said echo impulse representation device depending upon transmitted impulses of said ultra sound sender to visually represent echo ultra sound impulses produced by a transmitted impulse always during time of travel of next successive sent impulse in said precursor stretch, wherein said energizing means comprise a sweeping oscillator for frequency-modulating repetition frequency of transmitted impulse of said ultra sound sender, said actuating means comprising at least two monostable multivibrators connected in parallel between said ultra sound impulse sender and said echo impulses representation device, said monostable multivibrators being triggered alternately by successive transmitted impulses and producing, when triggered, an output impulse, said output impulse having the duration of the precursor time and at its end actuating said echo impulse representation device to visually represent echo impulses.

2. A device according to claim 1, further comprising at least one bistable multivibrator connected in front of said parallel monostable multivibrators, said bistable multivibrator in measure with transmitted impulses of said ultra sound impulse sender being alternately switched from its one stable condition to its other stable condition, and which when changing into one stable condition, triggers one monostable multivibrator, and when changing into the other stable condition, triggers the other monostable multivibrator.

3. A device according to claim 2 wherein, in case of precursor time periods which are smaller than the double of the echo impulse representation time at the echo impulse representation device, the average time distance between two sucessive transmitted impulses is equal to the sum of echo impulse representation time, sent impulse width and at least one half of frequency sweep width of the sweeping oscillator for frequency-modulating repetition frequency of transmitted impulse.

* * * * *